United States Patent [19]

Grasselli et al.

[11] 4,379,925

[45] Apr. 12, 1983

[54] LIQUID PHASE AMMOXIDATION OF CYCLOHEXANONE AND/OR CYCLOHEXANOL

[75] Inventors: Robert K. Grasselli, Chagrin Falls; Dev D. Suresh, Macedonia, both of Ohio; David R. Bridgeman, Wilmington, Del.

[73] Assignee: The Standard Oil Co., Cleveland, Ohio

[21] Appl. No.: 194,638

[22] Filed: Oct. 6, 1980

Related U.S. Application Data

[63] Continuation of Ser. No. 918,975, Jun. 26, 1978, abandoned.

[51] Int. Cl.³ .................. C07D 265/38; C07D 241/46; C07D 319/24
[52] U.S. Cl. .................................... 544/102; 544/347; 549/359
[58] Field of Search .............................. 544/102, 347; 260/340.3; 549/359

[56] References Cited

U.S. PATENT DOCUMENTS

| | | | |
|---|---|---|---|
| 3,154,562 | 10/1964 | Pursglove | 260/340.3 |
| 3,365,482 | 1/1968 | Khoobiar | 260/464 |
| 3,426,070 | 2/1969 | Doi et al. | 544/347 |
| 3,818,066 | 6/1974 | Barnett et al. | 260/465.3 |
| 3,907,860 | 9/1975 | Mee | 260/465.3 |

FOREIGN PATENT DOCUMENTS 1173773 10/1969 United Kingdom .

*Primary Examiner*—Paul M. Coughlan, Jr.
*Attorney, Agent, or Firm*—Emily A. Richeson; Herbert D. Knudsen; Larry W. Evans

[57] ABSTRACT

Cyclohexanone and/or cyclohexanol can be ammoxidized in the liquid phase to heterocyclic compounds by contacting the cyclohexanone and/or cyclohexanol with various oxidation catalysts in the presence of molecular oxygen and ammonia.

2 Claims, No Drawings

LIQUID PHASE AMMOXIDATION OF CYCLOHEXANONE AND/OR CYCLOHEXANOL

This is a continuation of application Ser. No. 918,975 filed June 26, 1978, now abandoned.

BACKGROUND OF THE INVENTION

The present invention relates to a novel ammoxidation reaction for converting cyclohexanone and/or cyclohexanol to various different heterocyclic compounds.

SUMMARY OF THE INVENTION

In accordance with the present invention, it has been found that cyclohexanone and/or cyclohexanol can be ammoxidized in the liquid phase to yield various aliphatic heterocyclic compounds of the following general formula:

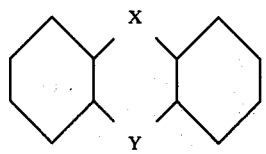

wherein X and Y are independently selected from the group consisting of —O—, and —N≡.

In these compounds, each of the terminal 6-membered rings may contain one or two ethylenically unsaturated bonds. Examples of compounds obtainable as reaction products are:

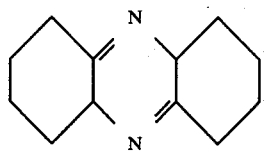

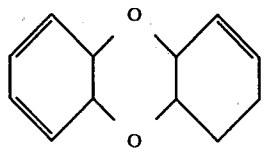

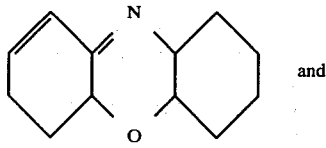

and

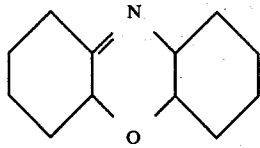

In accordance with the present invention, compounds of this structure are produced by contacting cyclohexanone and/or cyclohexanol with a suitable oxidation catalyst in the presence of molecular oxygen and ammonia, the reaction being carried out in the liquid phase. Moreover, it has been further found that analogs of cyclohexanone and/or cyclohexanol can be similarly ammoxidized to form corresponding aliphatic heterocyclic compounds.

Thus, the present invention provides a novel process for converting a cycloaliphatic ketone or alcohol containing 1 to 4 rings at least one of which is saturated to a reaction product comprising an aliphatic heterocyclic compound, the process comprising contacting the ketone or alcohol in the liquid phase with molecular oxygen, ammonia and a catalyst comprising at least one of an oxide, oxide mixture, oxide complex, heteropoly acid, heteropoly acid salt, isopolyacid or isopolyacid salt, of one or more elements selected from the group consisting of Mo, W, Sb and V.

DETAILED DESCRIPTION

In accordance with the present invention, cyclohexanone and/or cyclohexanol, as well as derivatives and analogs thereof can be ammoxidized to various aliphatic heterocyclic compounds. The primary reactant of the inventive process can be any cycloaliphatic ketone or alcohol wherein the oxygen is directly connected to a ring carbon. By cycloaliphatic is meant a ring-type compound which is at least partially saturated, and may be mononuclear or polynuclear, that is containing from 1 to 4 rings, in which the ring to which the oxygen atom is attached is at least partially saturated. These cycloaliphatic ketones and alcohols include those compounds which contain from 1 to 3 oxygen atoms each of which is directly connected to a ring carbon atom. The preferred cycloaliphatic compounds are the mononuclear naphthenic type compounds of the general formula $C_nH_{2n}$, where n is the integer 5 or 6. The especially preferred charge stock is cyclohexanone, cyclohexanol, and mixtures of the two. The ring compounds can have one or more groups attached to the ring which do not interfere with the ammoxidation reaction, such as lower alkyl having from 1 to 4 carbon atoms, phenyl, benzyl, tolyl, xylyl, etc. The charge stock compounds can suitably contain between 5 and 18 carbon atoms per molecule and preferably contain between 6 and 10 carbon atoms. Suitable charge stock compounds include the following without being limited, thereto, cyclohexanol,
cyclohexanone,
cyclohexanol,
cyclohexanone,
1,3-cyclohexanediol,
1,4-cyclohexanediol,
1,3-cyclohexanedione,
1,4-cyclohexanedione,
4-methylcyclohexanone,
4-t-butylcyclonexanol,
3,5-dimethylcyclohexanone,
4-phenylcyclohexanone,
3-tolycyclohexanone,
cyclopentanol,
cyclopentanone,
3-methylcyclopentanol,
2-ketotetraiin,
2-(1-cyclohexenyl)cyclohexanone,
2,6-dicyclohexenylcyclohexanone, etc.

Of course, when cyclopentanol and/or cyclopentanone or derivatives thereof are employed as the feed, the terminal alphatic rings on the reaction product will have 5 members, not 6.

The inventive process is carried out in the liquid phase, in either batch mode or continuous operation.

When the inventive process is carried out in the batch mode, the catalyst can be contacted with the reactants in any conventional manner. For example, a solid catalyst can be simply slurried in the liquid reactant. Alternatively, the catalyst can be dissolved in a solvent and the solution so obtained dissolved or dispersed in the liquid reactant. Or, if the solid catalyst is soluble in liquid reactant, it can be simply dissolved therein.

When the inventive process is carried out in a continuous manner, conventional techniques can be employed. For example, the liquid reactant can simply be passed over a bed of the catalyst to effect the appropriate contact.

In addition to the liquid reactant, molecular oxygen and ammonia must be supplied to the reaction system. Molecular oxygen can be supplied in any conventional form, such as pure $O_2$, air or the like. Ammonia can be supplied in a conventional manner. The molecular oxygen and ammonia can be fed to the reactor in which the reaction takes place individually, with each other, or together with the liquid reactant.

The amount of molecular oxygen and ammonia fed to the reactor can vary between wide limits. Also, the relative amount of molecular oxygen and ammonia controls the distribution of different aliphatic heterocyclic compounds contained in the reaction product. In general, the amount of molecular oxygen fed to the reaction system can vary between 0.1 to 20, preferably 0.2 to 5 mole, while the amount of ammonia fed to the reaction system can vary between 0.1 to 10, preferably 0.2 to 5 mole per mole of liquid reactant fed to the reactor. Also, the ratio of molecular oxygen to ammonia fed to the reactor is maintained in general between 1:10 to 10:0.01. In order to produce aliphatic heterocyclic compounds predominantly containing oxygen, the ratio of molecular oxygen to ammonia is preferably 10 to 0.01, most preferably 10 to 0.1, while molecular oxygen/$NH_3$ ratios on the order to 1 to 5, preferably 1 to 2 are normally employed if aliphatic heterocyclic compounds predominantly containing nitrogen are desired as reaction products.

The inventive process, as indicated above, is carried out in the liquid phase. To this end, the temperature of the reaction system is normally maintained so that the liquid reactant will remain a liquid at one atmosphere pressure. Although any reaction temperatures within this range can be employed, room temperature is preferred since it is easiest. The reaction can be carried out at superatmospheric and subatmospheric pressure as well as atmospheric pressure, but atmospheric pressure is preferred since it is also the easiest.

In addition to the above-indicated reactant, the reaction system can also contain various inert materials. For example, an inert gas such as nitrogen, helium, and so forth, can be admixed with the molecular oxygen if desired. Also, suitable inert liquids, such as for example a solvent for the catalyst, can also be present in the reaction system. So long as these materials are inert to the reactants, to the products and the catalysts, they can be easily tolerated by the inventive reaction system.

The catalysts useful in the inventive process are known oxidation and ammoxidation catalysts. They may be defined as solids which contain oxides of Mo, W, Sb, V or mixtures thereof, or oxide complexes of these materials. Catalysts of this type are generally believed in the art to be complex molybdates, tungstates, antimonates and vanadates. Heteropoly acids and isopolyacids (e.g. phosphomolybdic acid),, are also useful. Preferred catalysts contain at least one of the four foregoing elements and are preferably promoted with various additional elements such as P, B, As, Al, Bi, Te, Fe, Cr, Ni, Co, Cu, Mn, Sn, Ce, U and/or Th. The catalysts preferably have some acidic character.

Molybdate catalysts which are useful in the present invention can be generically described by the formula:

$$A_aB_bC_cD_dMo_eO_x$$

wherein
A is Cu, Fe, Ni, Co, Mn, U, Ce, Th, Ag or mixtures thereof;
B is V, P, Nb, Sb, As, B, Sn or mixtures thereof;
C is W, Cr or mixtures thereof;
D is alkali metal; earth alkali, Group IIB, Tl or mixtures thereof; and
wherein
a is 0 to 6;
b is 0.01 to 12;
c is 0 to 12;
d is 0 to 4;
e is 6 to 18; and
x is a number determined by the valence requirements of the other elements present.

Specific examples of such catalysts are:

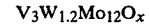
$V_3W_{1.2}Mo_{12}O_x$

$P_1Mo_{12}O_x$

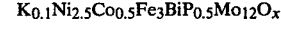
$K_{0.1}Ni_{2.5}Co_{0.5}Fe_3BiP_{0.5}Mo_{12}O_x$

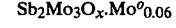
$Sb_2Mo_3O_x \cdot Mo^o{}_{0.06}$

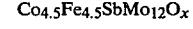
$Co_{4.5}Fe_{4.5}SbMo_{12}O_x$

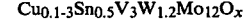
$Cu_{0.1-3}Sn_{0.5}V_3W_{1.2}Mo_{12}O_x$

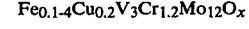
$Fe_{0.1-4}Cu_{0.2}V_3Cr_{1.2}Mo_{12}O_x$

$P_1Mo_{8-18}$

Another subgenus of molybdate catalysts useful in the present invention can be described by the following generic formula:

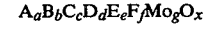
$$A_aB_bC_cD_dE_eF_fMo_gO_x$$

wherein
A is alkali metal, Tl, Sm or mixtures thereof;
B is Ni, Co, Mn, Mg, other earth alkaline, Group IIB elements, such as Zn or Cd;
C is Fe, Cr, Ce or mixtures thereof;
D is Bi or Te;
E is P, As, B, Sb, W or mixtures thereof;
F is Ge, Sn, Al, Ag, Au, Pb, Group VIII elements, V, Tl, In, Ta, rare earth metals or mixtures thereof; and
wherein
a is 0–4;
b is 0–20;
c is 0–20;
d is greater than 0–20;
e is 0–5;
f is 0–10
g is 6–18; and
x is a number determined by the valence requirements of the other elements present.

Specific examples of these catalysts are:

$MoO_x$ $Bi_aMo_bO_x$; (a,b=0.1-12)

$Fe_aBi_bMo_{12}O_x$; (a,b=0.01-20)

$Cr_aBi_bMo_{12}O_x$; (a,b=0.01-20)

$Bi_9PMo_{12}O_x$ $KFe_aCr_bW_cBi_dMo_{12}O_x$; (a,b,c=0.01-20)

$Fe_aTe_bMo_{12}O_x$; (a,b=0.01-20)

The tungstate type catalysts useful in accordance with the present invention can be selected from a wide variety of known tungstate oxidation catalysts. These catalysts can be described by the same generic formula used above in connection with the molybdate catalyst, the only difference being that tungsten is substituted for molybdenum in the above formulae (and if tungsten appears in the above formulae, it is correspondingly replaced by molybdenum). A particularly useful tungstate catalyst has the following formula:

$Bi_aW_bO_x$ wherein a is 0.1-12;

b is 0.1-12; and x is a number determined by the valence requirements of the other elements present.

Vanadate catalysts useful in accordance with the present invention can also be selected from a wide variety of known vanadate oxidation catalysts. These materials can also be described by the generic formulae given above in connection with molybdate type catalysts, the only difference being that vanadium is substituted for the molybdenum in the formulas (and if vanadium is present in the formula, it is correspondingly substituted by molybdenum). An example of a vanadate catalyst finding special use in the inventive process is given by the formula:

$Li_aPb_bV_cO_x$ wherein a is 0-2;

b and c are 0.01-12; and x is a number determined by the valence requirements of the other elements present.

The antimonate catalysts useful in the inventive process can also be selected from a wide variety of known antimonate oxidation catalysts. Basically, these catalysts are oxide complexes containing antimony and uranium; iron and antimony; or iron, uranium and antimony. These catalysts are described in a number of different patents, such as U.S. Pat. No. 3,197,419, U.S. Pat. No. 3,198,750, U.S. Pat. No. 3,338,952 and U.S. Pat. No. 3,431,292. These catalysts can be promoted with many different promoters such as tin, manganese, cerium, thorium, vanadium, cobalt, nickel, molybdenum, tungsten, iron and mixtures thereof. Combinations found especially useful are SnSb oxide, FeSb oxide, MnSb oxide, CeSb oxide, ThSb oxide, VSb oxide, CoSb oxide, NiSb oxide and mixtures thereof.

The catalyst employed in the inventive process may be used either in unsupported form or supported on a carrier. Any inert material known to be useful as a carrier in an oxidation reaction can be employed in the inventive process. Examples of useful carriers are $SiO_2$, $Al_2O_3$, $TiO_2$, $BPO_4$, $SbPO_4$, $ZrO_2$, Alundum balls and the like. The active catalyst material can be incorporated onto or into the carrier in any known technique. For example, the active catalyst material can be coated on the surfaces of the carrier, the active catalytic material can be impregnated into the carrier or the catalyst can be composed of discreet catalyst particles made up of a mixture of the active catalytic material and the carrier.

The reaction product produced by the present invention is obtained in the form of a liquid. This liquid normally contains a mixture of different aliphatic heterocyclic compounds as well as starting liquid reactant. These materials can be separated from one another by conventional techniques such as distillation, solvent extraction and fractional crystallization.

The aliphatic heterocyclic products of the inventive process are known and have many uses. For example, they can be easily pyrolized and/or pyrolitically oxydehydrogenated to yield analine, phenol, oxime, caprolactan and adiponitrile, which are well known commercial chemicals.

SPECIFIC EMBODIMENTS

In order to further describe the present invention, the following example is presented.

EXAMPLE 1

2 cc. of a solid catalyst comprising 50% $Bi_9PMo_{12}O_x$-50% $SiO_2$ was charged into a beaker containing 10 cc. cyclohexanone at room temperature to form a slurry of the catalyst in the cyclohexanone. $NH_3$ and air were bubbled through the slurry at a rate of 200 cc. $NH_3$ and 1600 cc. air per hour. The liquid in the beaker changed color from clear, through yellow to deep red in approximately 30 minutes. The reaction system was then removed from the catalyst and analyzed by gas chromatography and mass spectroscopy. The reaction product was found to contain the products listed in the following Table I in the amounts listed in Table I.

TABLE I

| Product | Molecular Weight | Amount (Weight %) |
|---|---|---|
| 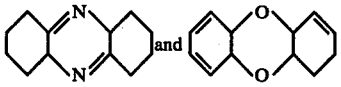 and 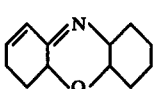 | 190 | ~38 |
| 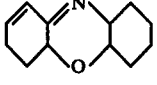 | 191 | ~25 |
| 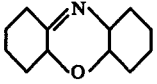 | 193 | ~5 |

Although only a few embodiments of the present invention have been described above, it should be appreciated that many modifications can be made without departing from the spirit and scope of the invention. All such modifications are intended to be included within the scope of the present invention, which is to be limited only by the following claims.

We claim:

1. A liquid phase ammoxidation process comprising contacting a reactant comprising a mononuclear cycloaliphatic ketone or alcohol, the cycloaliphatic moiety of said ketone or alcohol having the formula $C_nH_{2n}$ wherein n is 5 or 6, said cycloaliphatic ketone or alcohol being unsubstituted or substituted with at least one member selected from the group consisting of alkyl having 1 to 4 carbon atoms, phenyl, benzyl, tolyl, xylyl, said reactant containing 5 to 18 carbon atoms, in the liquid phase with molecular oxygen, ammonia and a molybdate catalyst of the following general formula:

$$A_aB_bC_cBi_d[E]P_eF_fMo_gO_x$$

wherein

A is alkali metal, Tl, Sm or mixtures thereof;

B is Ni, Co, Mn, Mg, other alkaline earths and Group IIB elements:

C is Fe, Cr, Ce or mixtures thereof;

F is Ge, Sn, Al, Ag, Au, Pb, Group VIII elements other than Ni, Co and Fe, V, Tl, In, Ta, rare earth metals or mixtures thereof; and wherein a is 0–4;

b is 0–20;

c is 0–20;

d is greater than 0–20;

e is greater than 0–5;

f is 0–10;

g is 6 to 18; and x is a number determined by the valence requirements of the other elements present.

2. The process of claim 1 wherein said ketone and/or alcohol is cyclohexanone and/or cyclohexanol.

* * * * *